United States Patent [19]

Daghighian et al.

[11] Patent Number: 5,338,937
[45] Date of Patent: Aug. 16, 1994

[54] RADIATION IMAGING DEVICE HAVING AN ENLARGED UNIFORM FIELD OF VIEW

[75] Inventors: Farhad Daghighian, New York; Saul Miodownik, West Hempstead; Peter Shenderov, Brooklyn; Behzad Eshaghian, New York, all of N.Y.

[73] Assignee: Sloan-Kettering Institute for Cancer Research, New York, N.Y.

[21] Appl. No.: 77,015

[22] Filed: Jun. 14, 1993

[51] Int. Cl.$^5$ .............................................. G01T 1/20
[52] U.S. Cl. .................................. 250/368; 250/369
[58] Field of Search .............. 250/368, 367, 366, 369, 250/361 R, 363.02, 363.03

[56] References Cited

U.S. PATENT DOCUMENTS

| | | | |
|---|---|---|---|
| 3,668,395 | 6/1972 | Walker | 250/363.02 |
| 4,075,485 | 2/1978 | Lijewski et al. | 250/369 |
| 4,180,737 | 12/1979 | Kingsley | 250/367 |
| 4,292,538 | 9/1981 | Carlson | 250/367 |
| 4,316,257 | 2/1982 | Del Medico et al. | 250/363.01 |
| 4,398,092 | 8/1983 | Carlson | 250/361 R |
| 4,459,486 | 7/1984 | Brunner et al. | 250/367 |
| 4,700,074 | 10/1987 | Bosnjakovic | 250/368 |
| 4,733,083 | 3/1988 | Wong | 250/368 |
| 4,764,678 | 8/1988 | Yamakawa | 250/361 R |
| 4,879,465 | 11/1989 | Persyk et al. | 250/363.02 |
| 4,990,785 | 2/1991 | Logan | 250/368 |
| 5,012,103 | 4/1991 | Tanaka et al. | 250/368 |

OTHER PUBLICATIONS

Abstract of Moore et al., *A Handheld, Lower Power, Gamma Camera: Design Considerations And Initial Results* The Journal of Nuclear Medicine (Supplement), vol. 29, No. 5, p. 832, May 1988.

"Crossed Wire Anoes Position-Sensitive Photomultiplier Tubes R2486 Series", Hamamatsu Technical Data Sheet, Oct., 1986.

*Primary Examiner*—Paul M. Dzierzynski
*Assistant Examiner*—Drew A. Dunn
*Attorney, Agent, or Firm*—John P. White

[57] ABSTRACT

A radiation imaging device of the type employing a scintillator and a position-sensitive photomultiplier tube eliminates or reduces edge effects and thereby increases the linear field of view by compensating for nonlinearities which distort an image close to the edge. Specifically, (1) a light guide is placed about the edge of the scintillator to channel light that would otherwise be reflected from the edge of scintillator to a light absorbing material so that edge reflected light is not detected by the position-sensitive photomultiplier tube and (2) variable resistors are employed to compensate for distortions in the image caused by current leakage along the edge of the position-sensitive photomultiplier tube.

11 Claims, 4 Drawing Sheets

RADIATION IMAGING DEVICE HAVING AN ENLARGED UNIFORM FIELD OF VIEW

FIELD OF THE INVENTION

This invention relates to a radiation imaging apparatus which has an enlarged uniform field of view because the edge effects which otherwise distort the image have been reduced or eliminated.

Within this application any publications which are referred to are referenced by arabic numbers enclosed within parentheses. Full citations for these and any other references may be found at the end of the specification immediately preceding the claims. The disclosures of all of these publications in their entireties are hereby incorporated by reference into this application in order to more fully describe the state of the art to which this invention pertains.

BACKGROUND OF THE INVENTION

One technique for detecting radiation is to use scintillation material to convert incident radiation into light. This light then can be measured by a light detector such as a photomultiplier tube. In applications where the location of the emitted radiation is important, as opposed to only determining the amount of radiation, a position-sensitive photomultiplier tube can be employed.

A position-sensitive photomultiplier tube converts light into electrons at a photocathode which is positioned across one end of the tube and multiplies the number of electrons through a series of parallel dynode meshes. The multiplied electrons impinge on one or more anode wires at the other end of the position-sensitive photomultiplier tube. Each anode wire is connect to one or more adjoining wires by resistors which form a resistor chain. When the electrons reach the anode wires the current at each end of the resistor chain changes. This current change is measured to pinpoint which anode wires are receiving the electrons. Accordingly, the corresponding position of the radiation which caused the light and subsequent electrons can be determined and displayed.

One application in which the field of view must be as large as possible is imaging radioactively labelled tissue for locating cancerous tumors in the body. This type of imaging has been performed with the imaging device scanning from outside the body. Since these newer imaging devices need to be placed in confined places, the size of the available field of view is particularly important.

One difficulty with the use of scintillators and position-sensitive photomultiplier tubes, however, is the edge effect. The edge effect is the loss of accurate position information for radiation received near the edges of the device. One cause of the edge effect is "edge packing". Edge packing occurs when the light emitted near the edge of the scintillation material is reflected off the edge of the scintillator to a position which does not correspond to where in the scintillation material the radiation was converted into light. Accordingly, this reflected light causes electrons to be generated and detected in the position-sensitive photomultiplier tube at positions different from where the radiation caused the light to be generated. For example, when part of the conical photon shower hits an insensitive area, the center of the mass of the registered signal is moved to the center of the position-sensitive photomultiplier tube.

One proposed solution to the edge packing problem is discussed in U.S. Pat. No. 4,990,785 to Logan. Logan discusses the placement of additional photomultipliers at the edge of the scintillation material so that the light will not be reflected, but instead will be measured separately. However, providing additional photomultiplier tubes increases the costs and size of the device. Size should be as small as possible for intraoperative use. Another proposed solution is to prevent the incident radiation from impinging on the edges of the scintillators by using collimators lacking holes near the edges, see for example, U.S. Pat. No. 3,668,395 to Walker, or by using collimators with long septa, see for example U.S. Pat. No. 4,180,737 to Kingsley. However, both these proposed solutions reduce the field of view by blocking some potentially non-reflecting radiation that would otherwise be received. Additionally, these solutions reduce the sensitivity of the camera by increasing the time required to form an image. Camera sensitivity is critically important for intraoperative applications since time is limited during surgery.

Another edge effect is due to current leakage within the position-sensitive photomultiplier tube. Specifically, some of the electrons leak out of the position-sensitive photomultiplier tube near the sides of the position-sensitive photomultiplier tube. Accordingly, since fewer electrons reach the anode wires which are closer to the edge of the position-sensitive photomultiplier tube than reach the other anode wires for the same amount of corresponding radiation, a distorted image which does not accurately reflect the received radiation near the edge of the device is displayed.

Although solutions to distorted images caused by other effects have been proposed, see for example U.S. Pat. No. 4,292,538 to Carlson, U.S. Pat. No. 4,398,092 to Carlson and U.S. Pat. No. 4,316,257 to Del Medico, the Carlson patents only discuss such correction for multiple detectors and Del Medico only discusses a software solution to correct for distortion.

SUMMARY OF THE INVENTION

The present invention overcomes these and other limitations by providing a light guide to channel light away from the edge of the scintillator and into a light absorbing material and by providing variable resistors near the ends of the resistor chains to compensate for the current leakage near the edge of the position-sensitive photomultiplier tube.

Specifically, this invention provides an imaging apparatus for creating images of radiation emitting objects having a scintillator for receiving radiation rays and converting the radiation rays into light signals, the scintillator having an edge, a position sensitive light signal detector optically connected to the scintillator for receiving the light signals, and a light guide positioned about the edge of the scintillator for channelling light signals which reach the edge of the scintillator away from the scintillator.

This invention also provides a light guide having an annular member having an inner edge surrounding and optically connected to the edge of the scintillator and an outer edge. This invention also provides an annular portion of the annular member located adjacent to a side of the position sensitive light signal detector. Also provided by this invention is a light guide formed from acrylic resin (LUCITE) and polished on all surfaces.

To absorb the light channelled away from the edge of the scintillator this invention provides a light absorbing material coating at least a portion of the outer edge of the light guide.

Also, this invention provides an imaging apparatus for creating images of radiation emitting objects having a position sensitive light signal detector for receiving light signals which correspond to radiation signals and for converting the light signals into electrons, a plurality of parallel anode wires for receiving electrons generated by the position sensitive light signal detector, a plurality of resistors, each resistor being connected between pairs of the anode wires to form a resistor chain, and means for adjusting the resistance of at least a portion of the plurality of resistors to compensate for greater current leakage near the edge of the position sensitive light signal detector.

This invention also provides a resistor chain having fixed resistors positioned between the pairs of the anode wires where the reception of the electrons is generally linear and variable resistors positioned where the reception of the electrons is generally non-linear.

Furthermore, this invention provides variable resistors positioned proximate the ends of the resistor chain and in one embodiment the number of variable resistors proximate each end of the resistor chain is four.

Also, this invention provides that the plurality of parallel anode wires can be one set of anode wires positioned perpendicular to another set of anode wires with each set having a separate resistor chain.

This invention also provides an imaging apparatus for creating images of radiation emitting objects having a scintillator for receiving radiation rays and converting the radiation rays into light signals, the scintillator having an edge, a position sensitive light signal detector optically connected to the scintillator for receiving the light signals, a light guide positioned about the edge of the scintillator for channelling light signals which reach the edge of the scintillator away from the edge of the scintillator, a plurality of parallel anode wires for receiving electrons, a plurality of resistors, each resistor being connected between pairs of the anode wires to form a resistor chain, and means for adjusting the resistance of at least a portion of the plurality of resistors to compensate for greater current leakage near the edge of the position sensitive light signal detector.

The features, objects and advantages of this invention are described in greater detail below in conjunction with the following drawings.

DETAILED DESCRIPTION OF THE INVENTION

This invention provides an imaging apparatus for creating images of radiation emitting objects having a scintillator for receiving radiation rays and converting the radiation rays into light signals, the scintillator having an edge, a position sensitive light signal detector optically connected to the scintillator for receiving the light signals, and a light guide positioned about the edge of the scintillator for channelling light signals which reach the edge of the scintillator away from the scintillator.

This invention also provides a light guide having an annular member having an inner edge surrounding and optically connected to the edge of the scintillator and an outer edge. This invention also provides an annular portion of the annular member located adjacent to a side of the position sensitive light signal detector. Also provided by this invention is a light guide formed from LUCITE and polished on all surfaces.

To absorb the light channelled away from the edge of the scintillator this invention provides a light absorbing material coating at least a portion of the outer edge of the light guide.

Also, this invention provides an imaging apparatus for creating images of radiation emitting objects having a position sensitive light signal detector for receiving light signals which correspond to radiation signals and for converting the light signals into electrons, a plurality of parallel anode wires for receiving electrons generated by the position sensitive light signal detector, a plurality of resistors, each resistor being connected between pairs of the anode wires to form a resistor chain, and means for adjusting the resistance of at least a portion of the plurality of resistors to compensate for greater current leakage near the edge of the position sensitive light signal detector.

This invention also provides a resistor chain having fixed resistors positioned between the pairs of the anode wires where the reception of the electrons is generally linear and variable resistors positioned where the reception of the electrons is generally non-linear.

Furthermore, this invention provides variable resistors positioned proximate the ends of the resistor chain and in one embodiment the number of variable resistors proximate each end of the resistor chain is four.

Also, this invention provides that the plurality of parallel anode wires can be one set of anode wires positioned perpendicular to another set of anode wires with each set having a separate resistor chain.

Figure 1:
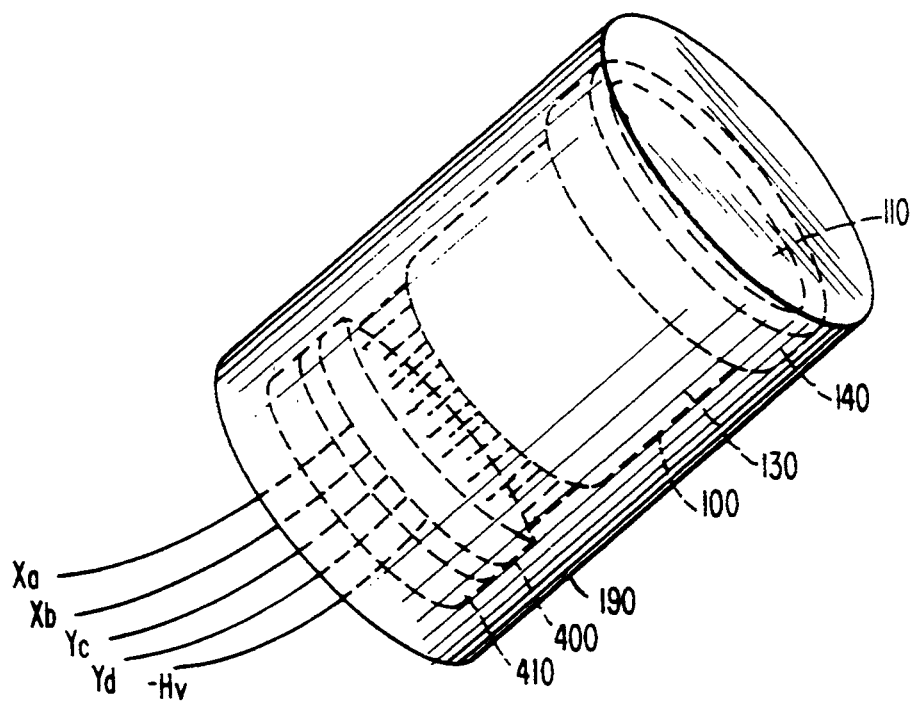
FIG. 1 is a perspective view of an imaging camera according to an embodiment of the subject invention.
Figure 2:
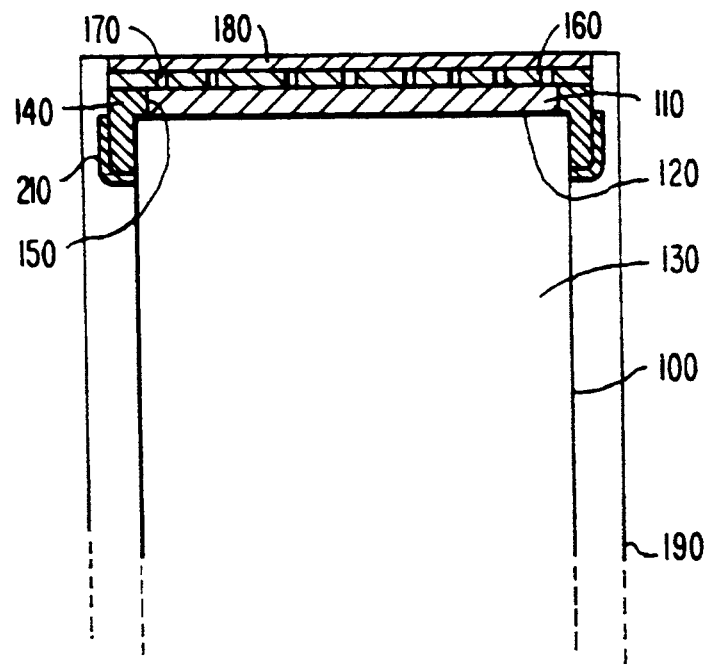
FIG. 2 is a cross-sectional view of an imaging camera according to an embodiment of the subject invention.

This invention also provides an imaging apparatus for creating images of radiation emitting objects having a scintillator for receiving radiation rays and converting the radiation rays into light signals, the scintillator having an edge, a position sensitive light signal detector optically connected to the scintillator for receiving the light signals, a light guide positioned about the edge of the scintillator for channelling light signals which reach the edge of the scintillator away from the edge of the scintillator, a plurality of parallel anode wires for receiving electrons, a plurality of resistors, each resistor being connected between pairs of the anode wires to form a resistor chain, and means for adjusting the resistance of at least a portion of the plurality of resistors to compensate for greater current leakage near the edge of the position sensitive light signal detector. FIGS. 1 and 2 illustrate a compact gamma ray imaging camera 100 designed to be used in an operating room to locate small tumors labelled with radioactive tumor tracers according to one embodiment of the subject invention.

This gamma ray imaging camera 100 is constructed from scintillation material 110 mounted on the front surface 120 of a position-sensitive photomultiplier tube 130. In this embodiment of the subject invention, the imaging camera 100 has approximately a 10 centimeter diameter and is 20 centimeters long. The scintillation material 110 is a 4 millimeter thick Cesium-Iodine-Thallium crystal having a 7 centimeter diameter. This crystal 110 is sensitive to gamma rays and does not have to be hermetically sealed. Also, in this embodiment of the subject invention, a multihole collimator 160 is used. The collimator 160 which is attached to the front of the scintillator is 25 millimeters thick and has hexagonally parallel holes 170 spaced 0.2 millimeters apart. Each hole 170 has a 3 millimeter diameter. Additionally, lead shielding 180 can be placed across the front of the collimator 160 to prevent or reduce background radiation.

To eliminate or reduce the edge packing effect, that is, the intensification of scintillation light near the edge of the scintillator caused by internal reflections of the light generated by the scintillator, a cylindrical collar is attached about the edge 150 of the scintillator 110 to act as a light guide 140. In one embodiment, the light guide 140 is made from acrylic resin (LUCITE) or transparent plastic although other materials may be used. With the light guide 140, light which impinges the edge 150 of the scintillator 110 and would otherwise be reflected back into the scintillator 110, instead is guided into the light guide 140 and away from scintillator 110. Also, to prevent the light which is guided away from being reflected within the light guide 140 and back into the scintillator 110, the outer edge of the light guide 140 is coated with a light absorbing material 210. In one embodiment the light absorbing material 210 is black paint, although other materials can be used.

In an embodiment of the subject invention, the light guide 140 has an "L"-shaped cross section so that the edge-impinging light travels through the light guide 140 around the edge of the adjacent position-sensitive photomultiplier tube 130 before being absorbed by the light absorbing material 210. Since the side of the position-sensitive photomultiplier tube is impervious to light, the chance that the light will be reflected within the light guide 140 and back into the scintillator 110 is reduced further. Also, the shape of the light guide is such that it keeps the size of the camera to a minimum.

A compact housing 190 which is constructed from stainless steel is used in one embodiment of the subject invention to contain the camera 100, collimator 160, lead shielding 180, light guide 140, some electronics 400 and a high voltage power supply 410. However, the housing and shieldings can be made of other materials such as tungsten.

Figure 3:
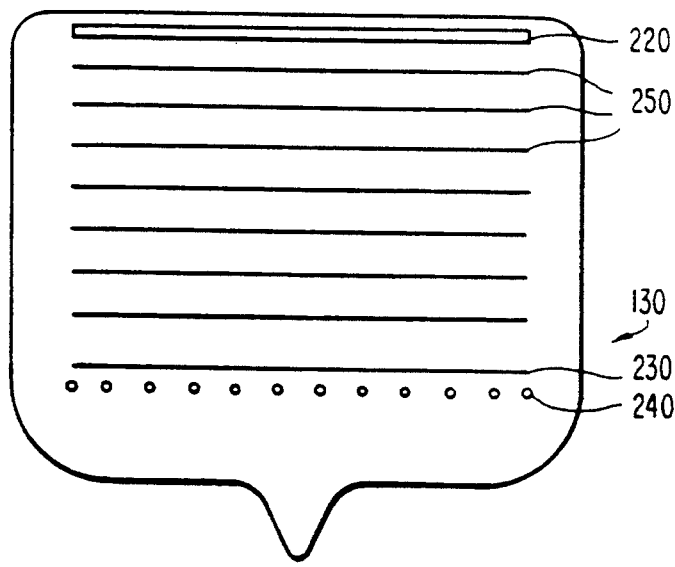
FIG. 3 is a cross-sectional view of a position-sensitive photomultiplier tube according to an embodiment of the subject invention.

As illustrated in FIG. 3 the position-sensitive photomultiplier tube 130 in the gamma imaging camera 100 is constructed with a photocathode 220 at one end for converting the light emitted by the scintillator 110 into electrons and two sets of parallel anode wires at the other end 230, 240. One set of parallel anode wires 230 defines points along an X-axis and the other set 240, being perpendicular to the first set, defines points along a Y-axis. A series of proximity mesh dynodes 250 are placed between the photocathode 220 and the anode wire sets 230, 240 to multiply the number of electrons so that the signals are strengthened for better detection. To determine the position of the incident electrons, one end of each anode wire 260 is connected to a node 270 in a resistor chain 280. Accordingly, the ratio of the difference of the currents measured at each end of a resistor chain 280 to the sum of these currents yields the proportional position of the electrons impinging the anode wire set 230, 240 attached to that resistor chain 280 during a particular sample time.

Figure 5:
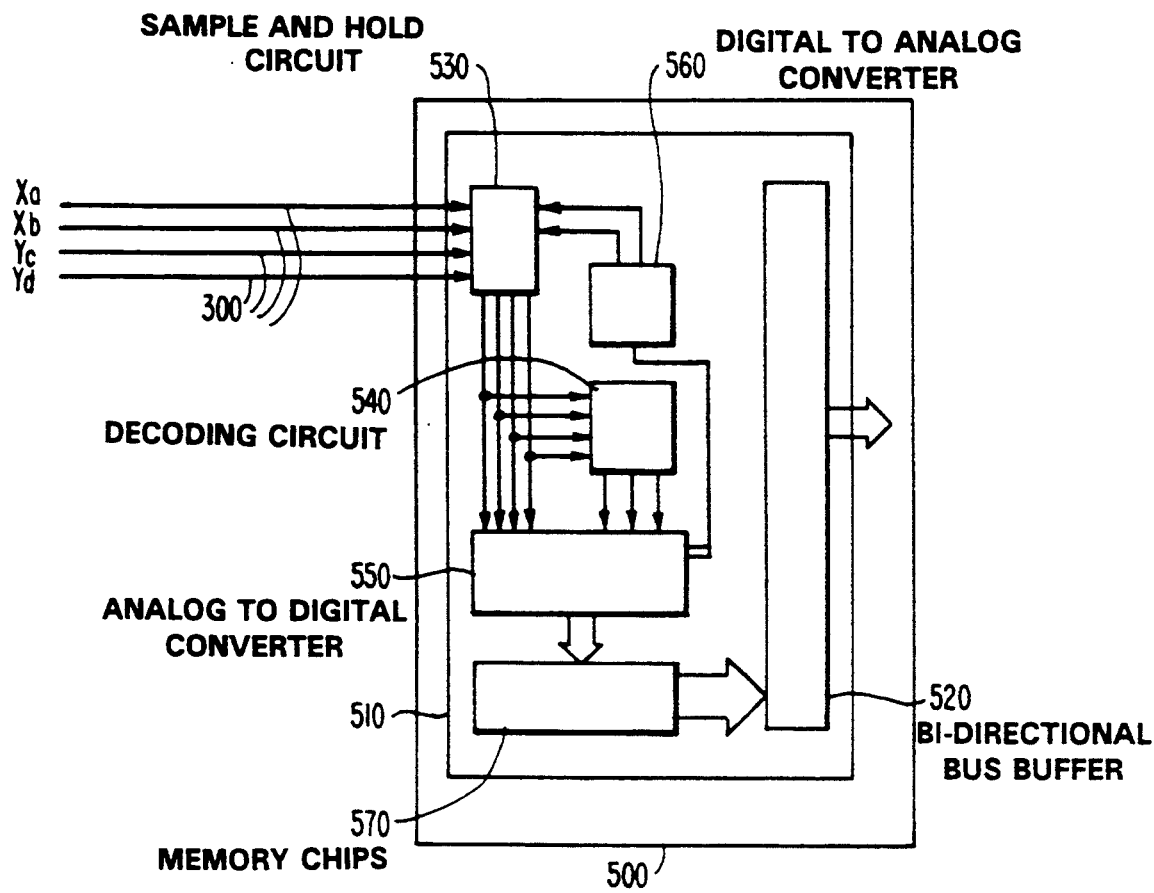
FIG. 5 is a block diagram of the electronic circuit of an embodiment of the subject invention.

Each end of each resistor chain 280 is connected to an amplifier 290 and the output of each amplifier 290 is connected by an electrical conduit 300 to an electronic circuit, see FIG. 5, which further amplifies and digitizes the four signals from the two axes. The digitized signals are sent to a computer 500 from which the coordinates of the scintillation events can be analyzed and imaged.

More specifically, if all the resistors in a resistor chain are equal, the proportional position of the impinging electrons detected along one axis, Xk, in a position-sensitive photomultiplier tube having N resistors along the X axis can be calculated as:

$$Xk=(Xa-Xb)/(Xa+Xb)$$

where Xa and Xb are currents or voltages at each end of a resistor chain. Additionally, since the electric charge from the k-th anode is divided between the two ends of the resistor chain according to the ratio of:

$$Xb/Xa=k/(N-k)$$

the proportional position of the corresponding scintillation event can be represented as:

$$Xk=(N-2k)/N.$$

However, because some electrons leak out near the edges of a position-sensitive photo-multiplier tube while the electrons are being multiplied, the proportional position of a scintillation event close to the edge becomes distorted, that is, the detected signal on an anode wire near the edge is not as strong as the detected signal on an anode wire nearer the center for the same amount of corresponding scintillator light. This distortion of proportional position can be represented as:

$$Xk=(N-2k\pm d)/N$$

where d is the deviation caused by the current leakage. This deviation differs from one photomultiplier tube to another and is usually different for the x direction and the y direction.

Figure 4:
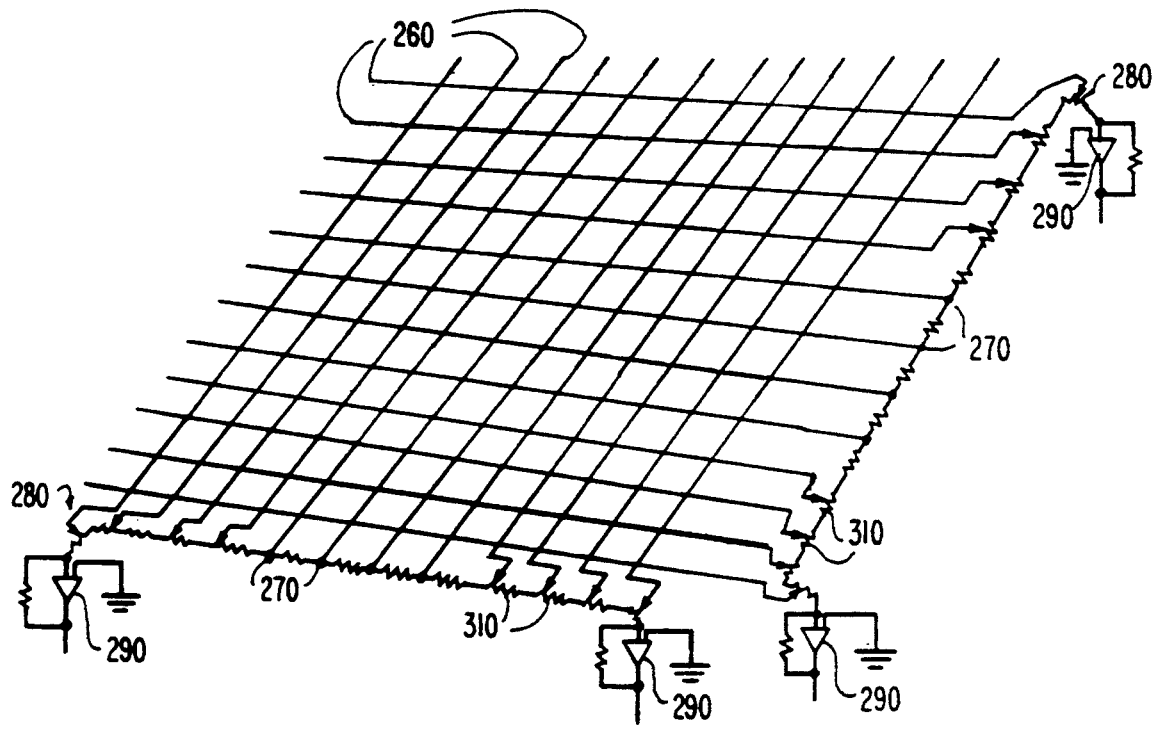
FIG. 4 is a perspective view of two sets of anode wires and resistor chains according to an embodiment of the subject invention.
Figure 6:
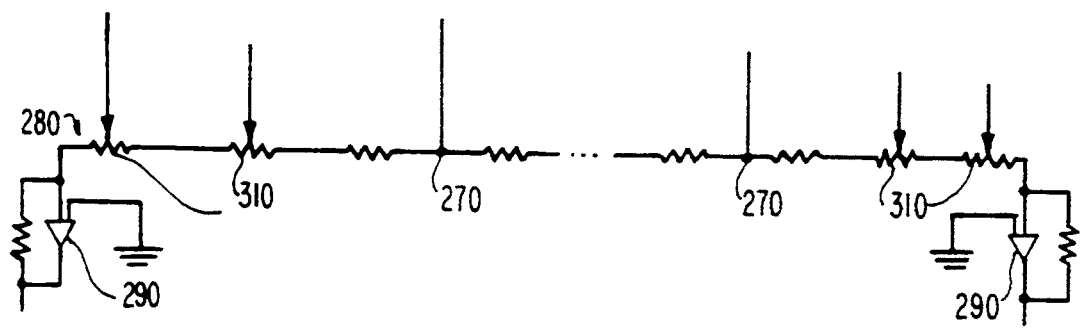
FIG. 6 is a circuit diagram of a resistor chain and anode wires according to an embodiment of the subject invention.
Figure 7:
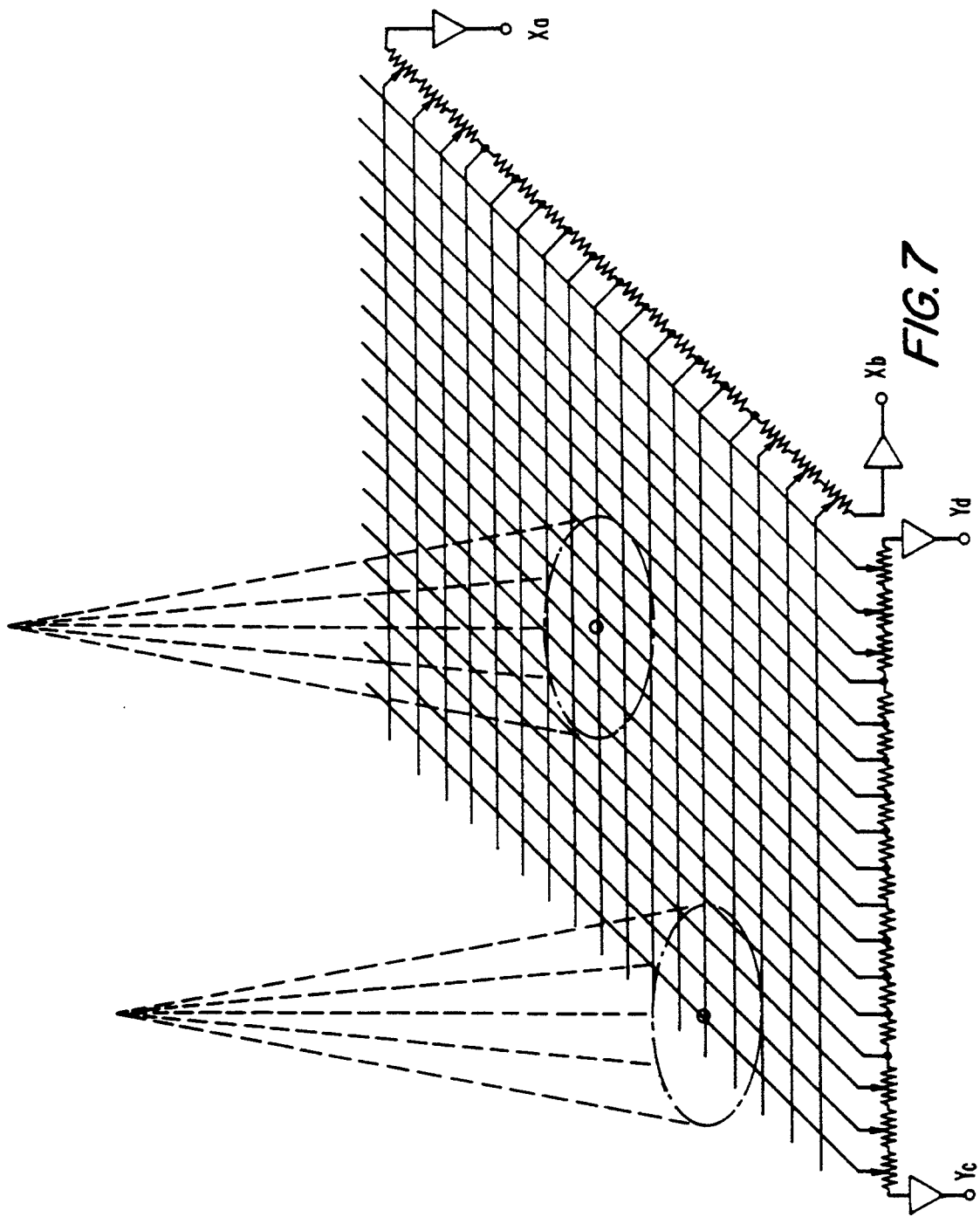
FIG. 7 is a perspective view of two sets of anode wires and resistor chains of an embodiment of the subject invention being hit with electrons at two positions.

To eliminate or reduce the distortion caused by the current leakage and thereby increase the useable surface area of the position-sensitive photomultiplier tube 130 in an embodiment of the subject invention, see FIGS. 4, 6 and 7 the resistor chains 280 attached to the anode wires 260 are modified by using adjustable resistors 310 at the extremities of each resistor chain 280. Only the resistors near the edge of the position-sensitive photomultiplier tube 130 need to be made adjustable because the central part of the position-sensitive photomultiplier tube 130 typically has a linear response. However, the subject invention envisions the use of adjustable resistors 310 to correct defects similar to current leakage wherever they occur in a position-sensitive photomultiplier tube 130.

In one embodiment of the subject invention, a position-sensitive photomultiplier tube 130 having only the last four resistors on each end of a resistor chain 280 being adjustable was found to be sufficient to correct for current leakage distortions near the edge. Once these four adjustable resistors or potentiometers 310 are set for the individual leakage characteristics of a particular position-sensitive photomultiplier tube 130, the total resistance of the resistor chain 280 remains constant.

The electronic circuitry of an embodiment of the subject invention is discussed with reference to FIG. 5. The electronic circuit and imaging system are based on an image acquisition system using an IBM-compatible PC, although any commercially available computer could be used. The image acquisition system consists of a computer 500 and a circuit board 510. The circuit board 510 includes a bi-directional bus buffer 520 along with programmed array logic chips to decode addresses and control bus signals. This circuit board also contains a sample and hold circuit 530, a decoding circuit 540, an analog-to-digital converter 550, a digital-to-analog converter 560 and memory chips 570. The sample and hold circuit 530 receives the four signals amplified by the preamplifiers 290 which amplify the signals from the resistor chains 280 mounted on the rear of the position-sensitive photomultiplier tube 130. The sample and hold circuit 530 converts these relatively short pulses of amplified position component signals (Xa, Xb, Yc, Yd) into constant signals with longer durations so that the signals can be digitized. The decoding circuit 540 calculates the coordinates (X,Y) of the event from these amplified signals (Xa, Xb, Yc, Yd) according to the following equations: $X=(Xa-Xb)/(Xa+Xb)$ and $Y=-(Yc-Yd)/(Yc+Yd)$. The decoding circuit also calculates $Z=Xa+Xb+Yc+Yd$, which is a measure of the energy deposited by the incident radiation. The analog-to-digital converter 550 is a CMOS high speed, 8-channel, 8-bit type so that the computer can access the four position component signals, decoded X and Y signals, as well as an energy proportional signal. Having these signals digitized and acquired by the personal computer makes the system very flexible. The upper and the lower energy thresholds are set through software using the digital-to-analog converter 560. This allows imaging of only those scintillation events that fall within the preset energy window. Also, intermediate memory chips 570 are employed on the data acquisition board 510 to store information and speed up the system.

The software for controlling the computer 500 and its image acquisition system in one embodiment is written in Microsoft C and Quick BASIC which are relatively fast and easy to use. However, any other computer language may be used. The software allows substantial manipulation of the images. For example, color images, energy spectrums and radioactive concentration profiles can be displayed. Also, one or more images can be focused, shifted, added and/or subtracted. Additionally, other non-uniformities and non-linearities in the images can be corrected.

A miniature high voltage power supply 410 (Hamamatsu C1309-06) is mounted behind the position-sensitive photomultiplier tube 130. This whole assembly can be encased in a DELRIN type material jacket. This instrument, like other instruments, is placed in a sterile bag during the surgery. In order to ensure the electrical safety of the patient and operators during surgery, all high voltage components are insulated from any metal component within the assembly. KAPTON high voltage insulating sheeting is formed around the position-sensitive photomultiplier tube 130, the high voltage power supply 410 and all the related electronics. All the hand held units are sealed with silicone rubber to prevent the entry of moisture that might compromise the operation and safety of the instrument. Additionally, the unit is designed to ensure compliance with the AAMI/ANSI ESI-1985 Safe Current Limits For Electromedical Apparatus.

To use this imaging camera 100, a patient is injected with a substance which has a radioactive marker before the surgical procedure begins. A particular radiolabelled substance is chosen because of the properties that cause the particular substance to accumulate in the tumor or tumors at higher amounts than in other tissue. For example, to locate tumors in lung tissue the radiopharmaceutical bleomycin labelled with Cobalt-57, a gamma ray emitter, has been found to be effective, see Barber et al (1).

After the radioactively labelled substance has been given sufficient time to reach the tumors, the scintillator end of the imaging camera 100 is moved about the body, either inside or outside, to locate tumors. Most of the radiation which reaches the surface of the scintillator 110, generates light which travels directly through the front surface 120 of the position-sensitive photomultiplier tube 130 to the photocathode 220. However, light generated by the scintillator 110 which travels to the edge 150 of the scintillator 110 is channelled away from the scintillator 110 by the collar 140. This channelled light is absorbed by black paint 210 at the edge 150 of the collar 140 and thus cannot be reflected back into the scintillator 110 where the errant light might reach the photocathode 220 and generate errant electrons. Accordingly, the photocathode 220 only generates electrons which correspond to light which is not reflected from the edge 150 of the scintillator 110. As the electrons travel through the position-sensitive photomultiplier tube 130 to the sets of anode wires 230, 240 the number of electrons is multiplied by the series of parallel dynode meshes 250. When the multiplied electrons impinge on the anode wires 230, 240 current is generated. The current flows to the ends of the resistor chains 280 which can be used to calculate the location of the multiplied electrons received during a selected sample time. To compensate for electrons that leak out the edge of the position-sensitive photomultiplier tube 130, the variable resistors 310 at the ends of the resistor chains 280 are adjusted. This adjustment must be made individually for each position-sensitive photomultiplier tube because each position-sensitive photomultiplier tube has different amounts of current leakage.

Experimental results show that using the adjustable resistors 310 yields about a 10% increase in the diameter of the uniform signal surface area. Specifically, the uniformity was tested by flooding the compact gamma ray imaging camera 100 with gamma rays emitted from a Technium-99m source placed two meters away from the imaging camera 100. This resulted in a +10% change in the unmodified 5 centimeter diameter field of view. In combination with the LUCITE collar 140 and other techniques, the field of view has been increased to 5.8 centimeters with a uniformity of better than ±5%.

In preliminary tests, a phantom consisting of multiple holes drilled in a flat LUCITE block was used. These holes, 2 millimeters in depth and diameter, were placed 12 millimeters apart from each other and were filled with unequal amounts of Technium-99m in solution. The phantom was placed 5 centimeters away from the face of the gamma ray imaging camera's collimator 160 and an image was acquired. Subsequent analysis of this image intensity profile yielded a full width at half maximum (FWHM) of 5 millimeters.

Even though most of the embodiments discussed above referred to the use of the subject invention for imaging gamma rays, it should be understood that the subject invention can also be employed for imaging other types of radiation, such as, for example, beta rays and X-rays. These other cameras would differ in the type of scintillator, collimator and shielding used.

Although this invention has been described with respect to specific embodiments, many variations based on these specific embodiments can be made by a person of ordinary skill in the art without departing from the spirit of the disclosure or the scope of the appended claims. The embodiments are presented for the purposes of illustration only and should not be read as limiting the invention or its application. Therefore, the claims should be interpreted commensurate with the spirit and scope of the invention.

REFERENCES (1) Barber et al., *Small Radiation Detectors For Bronchoscopic Tumor Localization* IEEE Transactions on Nuclear Science, Vol. NS-27, No. 1, pp. 496–502, February, 1980.

We claim:

1. An imaging apparatus for creating images of radiation emitting objects comprising:
    a scintillator for receiving radiation rays and converting the radiation rays into light signals, the scintillator having an edge;
    a position sensitive light signal detector optically connected to the scintillator for receiving the light signals; and
    a light guide positioned about the edge of the scintillator for channelling light signals which reach the edge of the scintillator away from the scintillator such that the channeled light signals are not received by the position sensitive light signal detector.

2. An imaging apparatus according to claim 1, wherein the light guide comprises:
    an annular member having an inner edge surrounding and optically connected to the edge of the scintillator and an outer edge.

3. An imaging apparatus according to claim 2, wherein the annular member further comprises:
    an annular portion located adjacent to a side of the position sensitive light signal detector.

4. An imaging apparatus according to claim 2, wherein the light guide is formed from an acrylic resin and is polished on all surfaces.

5. An imaging apparatus according to claim 2, wherein the light guide further comprises:
    a light absorbing material coating at least a portion of the outer edge.

6. An imaging apparatus for creating images of radiation emitting objects, comprising:
    a position sensitive light signal detector for receiving light signals which correspond to radiation signals and for converting the light signals into electrons;
    a plurality of parallel anode wires for receiving electrons generated by the position sensitive light signal detector;
    a plurality of resistors, each resistor being connected between pairs of the anode wires to form a resistor chain; and
    means for adjusting the resistance of at least a portion of the plurality of resistors to compensate for greater current leakage near an edge of the position sensitive light signal detector.

7. An imaging apparatus according to claim 6, wherein the resistor chain comprises:
    fixed resistors positioned between the pairs of the anode wires where the reception of the electrons is generally linear; and
    variable resistors positioned where the reception of the electrons is generally non-linear.

8. An imaging apparatus according to claim 7, wherein the variable resistors are positioned proximate the ends of the resistor chain.

9. An imaging apparatus according to claim 8, wherein the number of variable resistors proximate each end of the resistor chain is four.

10. An imaging apparatus according to claim 6, wherein the plurality of parallel anode wires comprises one set of anode wires positioned perpendicular to another set of anode wires and each set has a separate resistor chain.

11. An imaging apparatus for creating images of radiation emitting objects, comprising:
    a scintillator for receiving radiation rays and converting the radiation rays into light signals, the scintillator having an edge;
    a position sensitive light signal detector optically connected to the scintillator for receiving the light signals;
    a light guide positioned about the edge of the scintillator for channelling light signals which reach the edge of the scintillator away from the edge of the scintillator such that the channeled light signals are not received by the position sensitive light signal detector;
    a plurality of parallel anode wires for receiving electrons;
    a plurality of resistors, each resistor being connected between pairs of the anode wires to form a resistor chain; and
    means for adjusting the resistance of at least a portion of the plurality of resistors to compensate for greater current leakage near the edge of the position sensitive light signal detector.

* * * * *